United States Patent [19]

Murakami et al.

[11] Patent Number: 5,669,895
[45] Date of Patent: Sep. 23, 1997

[54] ABSORBENT ARTICLE HAVING RAPID DISTRIBUTION STRIP

[75] Inventors: Setsuko Murakami, Yamanashi; Yumi Masuda, Kobe, both of Japan

[73] Assignee: The Procter & Gamble Company, Cincinnati, Ohio

[21] Appl. No.: 232,243

[22] PCT Filed: Nov. 6, 1992

[86] PCT No.: PCT/US92/09717

§ 371 Date: Sep. 29, 1994

§ 102(e) Date: Sep. 29, 1994

[87] PCT Pub. No.: WO93/09745

PCT Pub. Date: May 27, 1993

[30] Foreign Application Priority Data

Nov. 11, 1991 [JP] Japan ................................. 3-294665

[51] Int. Cl.$^6$ .................................................. A61F 13/15
[52] U.S. Cl. .......................... 604/380; 604/378; 604/379; 604/358
[58] Field of Search ............................... 604/378, 379, 604/358, 380, 383, 384

[56] References Cited

U.S. PATENT DOCUMENTS

| | | |
|---|---|---|
| Re. 26,515 | 1/1969 | Holliday et al. . |
| Re. 32,649 | 4/1988 | Brandt et al. . |
| 1,946,626 | 2/1934 | Jurgensen . |
| 2,296,341 | 9/1942 | Fourness . |
| 2,548,341 | 4/1951 | Bricmont . |
| 2,551,663 | 5/1951 | Fox . |
| 2,929,179 | 3/1960 | George . |
| 3,095,878 | 7/1963 | Bassett . |
| 3,343,543 | 9/1967 | Glassman . |
| 3,356,092 | 12/1967 | Joa . |
| 3,386,442 | 6/1968 | Sabee . |
| 3,397,697 | 8/1968 | Rickard . |
| 3,406,688 | 10/1968 | Cubitt . |
| 3,431,911 | 3/1969 | Meisel . |
| 3,523,535 | 8/1970 | Croon et al. . |
| 3,528,421 | 9/1970 | Vaillancourt et al. . |
| 3,572,342 | 3/1971 | Lindquist et al. . |
| 3,593,717 | 7/1971 | Jones ............................ 604/378 |
| 3,604,422 | 9/1971 | Sabee . |
| 3,651,809 | 3/1972 | Champaigne, Jr. . |
| 3,695,269 | 10/1972 | Malaney . |
| 3,716,430 | 2/1973 | Croon et al. . |
| 3,736,931 | 6/1973 | Glassman . |
| 3,799,167 | 3/1974 | Miller et al. . |
| 3,815,602 | 6/1974 | Johns et al. . |
| 3,825,006 | 7/1974 | Ralph . |
| 3,838,693 | 10/1974 | Sherman . |
| 3,844,288 | 10/1974 | Kiela . |
| 3,871,037 | 3/1975 | Willington . |
| 3,954,721 | 5/1976 | Gross . |
| 3,983,095 | 9/1976 | Bashaw et al. . |
| 3,996,936 | 12/1976 | Widlund et al. . |
| 4,050,462 | 9/1977 | Woon et al. . |
| 4,136,697 | 1/1979 | Smith . |
| 4,211,227 | 7/1980 | Anderson et al. . |
| 4,231,357 | 11/1980 | Hessner . |
| 4,285,342 | 8/1981 | Mesek . |
| 4,287,251 | 9/1981 | King et al. . |
| 4,324,246 | 4/1982 | Mullane et al. . |
| 4,335,722 | 6/1982 | Jackson . |
| 4,338,371 | 7/1982 | Dawn et al. . |
| 4,360,022 | 11/1982 | Usami et al. . |
| 4,364,992 | 12/1982 | Ito et al. . |
| 4,397,644 | 8/1983 | Matthews et al. . |
| 4,410,324 | 10/1983 | Sabee . |
| 4,411,660 | 10/1983 | Dawn et al. . |
| 4,443,512 | 4/1984 | Deluaux ........................ 604/379 |
| 4,500,315 | 2/1985 | Pieniak et al. . |
| 4,536,181 | 8/1985 | Cook . |
| 4,537,590 | 8/1985 | Peiniak et al. . |
| 4,557,777 | 12/1985 | Sabee . |
| 4,579,556 | 4/1986 | McFarland . |
| 4,610,678 | 9/1986 | Weisman et al. . |
| 4,655,757 | 4/1987 | McFarland et al. . |
| 4,666,439 | 5/1987 | Williams et al. . |
| 4,673,402 | 6/1987 | Weisman et al. . |
| 4,676,784 | 6/1987 | Erdman et al. . |
| 4,681,577 | 7/1987 | Stern et al. . |
| 4,685,914 | 8/1987 | Holtman . |
| 4,699,823 | 10/1987 | Kellenberger et al. . |
| 4,701,177 | 10/1987 | Ellis et al. . |
| 4,762,520 | 8/1988 | Wallstrom . |
| 4,769,022 | 9/1988 | Chang et al. . |
| 4,781,710 | 11/1988 | Megison et al. ................ 604/378 |
| 4,781,711 | 11/1988 | Houghton et al. . |

| | | |
|---|---|---|
| 4,787,896 | 11/1988 | Houghton et al. . |
| 4,798,603 | 1/1989 | Meyer et al. . |
| 4,855,179 | 8/1989 | Bourland et al. . |
| 4,880,419 | 11/1989 | Ness . |
| 4,888,238 | 12/1989 | Katz et al. . |
| 4,892,535 | 1/1990 | Bjornberg et al. ............ 604/380 |
| 4,900,318 | 2/1990 | Toth . |
| 4,923,454 | 5/1990 | Seymour et al. . |
| 4,935,022 | 6/1990 | Lash et al. . |
| 4,936,839 | 6/1990 | Molee et al. ............ 604/378 |
| 4,938,754 | 7/1990 | Mesek . |
| 4,950,262 | 8/1990 | Takagi . |
| 4,988,344 | 1/1991 | Reising et al. . |
| 4,988,345 | 1/1991 | Reising . |
| 4,990,147 | 2/1991 | Freeland . |
| 5,013,309 | 5/1991 | Baigas, Jr. et al. . |
| 5,037,409 | 8/1991 | Chen et al. . |
| 5,061,259 | 10/1991 | Goldman et al. . |
| 5,061,260 | 10/1991 | Callahan et al. . |
| 5,092,860 | 3/1992 | Pigneul . |
| 5,098,422 | 3/1992 | Davis et al. . |
| 5,128,193 | 7/1992 | Anapol et al. ............ 604/379 |
| 5,147,345 | 9/1992 | Young et al. . |
| 5,149,335 | 9/1992 | Kellenberger et al. . |
| 5,175,046 | 12/1992 | Nguyen . |
| 5,176,668 | 1/1993 | Bernardin . |
| 5,192,606 | 3/1993 | Proxmire et al. . |
| 5,200,248 | 4/1993 | Thompson et al. . |
| 5,217,445 | 6/1993 | Young et al. . |
| 5,300,054 | 4/1994 | Feist et al. . |
| 5,360,420 | 11/1994 | Cook et al. ............ 604/378 |

FOREIGN PATENT DOCUMENTS

| | | |
|---|---|---|
| 254 476 | 1/1988 | European Pat. Off. . |
| 0291316 | 11/1988 | European Pat. Off. . |
| 0 291 316 | 11/1988 | European Pat. Off. . |
| 0 339 461 | 11/1989 | European Pat. Off. . |
| 0 343 941 | 11/1989 | European Pat. Off. . |
| 391 814 A2 | 4/1990 | European Pat. Off. . |
| 0 397 110 A2 | 11/1990 | European Pat. Off. . |
| 0 399 564 A | 11/1990 | European Pat. Off. . |
| 0 414 541 | 2/1991 | European Pat. Off. . |
| 0 443 627 A2 | 8/1991 | European Pat. Off. . |
| 3917791 | 12/1990 | Germany . |
| A-4024053 | 1/1992 | Germany . |
| 2 078 527 | 1/1962 | United Kingdom . |
| WO 89/01325 | 2/1989 | WIPO . |
| WO 90/05514 | 5/1990 | WIPO . |
| WO 90/14813 | 12/1990 | WIPO . |
| WO 91/11165 | 8/1991 | WIPO . |
| WO 91/11162 | 8/1991 | WIPO . |
| WO 91/1164 | 8/1991 | WIPO . |
| WO 91/11163 | 8/1991 | WIPO . |

*Primary Examiner*—John G. Weiss
*Assistant Examiner*—Dennis Ruhl
*Attorney, Agent, or Firm*—Edward J. Milbrada; Jeffrey V. Bamber; Steven W. Miller

[57] ABSTRACT

An absorbent article such as a sanitary napkin having a liquid distribution strip that provides improved distribution or wicking of liquid exudates. The absorbent article comprises a liquid permeable topsheet, a liquid impermeable backsheet, a liquid absorbent pad and a liquid distribution strip. The absorbent pad is positioned between the topsheet and the backsheet. The liquid distribution strip is positioned between the topsheet and the absorbent pad. The liquid distribution strip comprises a nonwoven web which has a screen pattern having high fiber density portions with reduced spacing between the fibers and/or an embossed pattern having a highly compressed portion. The high fiber density portion of the screen pattern is oriented primarily to the longitudinal ends of the absorbent pad so as to distribute the liquid exuded to the longitudinal ends. The highly compressed portions of the embossed pattern are oriented primarily to the longitudinal ends so as to inhibit the distribution of liquid toward the lateral edges.

7 Claims, 4 Drawing Sheets

ABSORBENT ARTICLE HAVING RAPID DISTRIBUTION STRIP

This application is a 371 of PCT/US92/09717 filed Nov. 6, 1992, which is the PCT filing of Japanese application 294665 filed Nov. 11, 1991.

FIELD OF THE INVENTION

This invention relates to a novel absorbent article, particularly to a sanitary article such as a sanitary napkin or an absorbing sheet. As used herein, the term "absorbent article" refers to devices which absorb and contain body exudes, and, more specifically, refers to devices which are placed against or in proximity to the body of the wearer to absorb and contain the various liquid exudates discharged from the body.

BACKGROUND OF THE INVENTION

All manner and variety of absorbent articles configured for the absorption of body exuded (liquids or fluids) such as menses, urine, and feces are, of course, known. Generally, an absorbent article comprises a liquid pervious topsheet, a liquid impervious backsheet, and an absorbent core or pad positioned between the topsheet and the backsheet. The exudates from a wearer's body readily penetrate through the topsheet and are contained in the absorbent core. An additional layer or layers can also be interposed between any of these layers. Such additional layers can provide a rapid distribution of the exudates.

Such distribution layers improve wicking of exudates over and into the absorbent core. There are several reasons why the improved wicking of liquid exudates is important, including providing a more even distribution of the liquid exudates throughout the absorbent core and allowing the absorbent article to be made relatively thin. The wicking referred to herein can encompass the transportation of liquids in one, two or all directions (i.e., in the x-y plane and/or in the z-direction). The distribution layer can comprise several different materials including nonwoven or woven webs of synthetic fibers. Several references describe absorbent products having layers for such purpose. Examples of sanitary napkins having an acquisition layer and a topsheet are more fully described in U.S. Pat. No. 4,950,264 issued to Osborn, and U.S. patent application Ser. No. 07/810,774, "Absorbent Article Having Fused Layers", filed Dec. 17, 1991 now abandoned in the names of Cree, et al. Each of these references are incorporated herein by reference.

However, there is need for a much improved liquid distribution layer having a high liquid diffusion rate in a longitudinal direction. That is, the diffusion speed of nonwovens is generally constant irrespective of direction. When nonwoven material in general is used as an absorbent core cover sheet or as a topsheet in a sanitary napkin, a large amount of liquid can be wicked in the lateral (width) direction. Side leakage can sometimes result when the liquid absorption capacity in the lateral sides of the absorbent core is exceeded.

Therefore, it is an object of the present invention to provide a liquid distribution strip having improved wicking, and superior liquid distribution to the longitudinal ends of the sanitary napkin. It is also an object of the present invention to provide a liquid distribution strip having inhibited liquid distribution to the sides of the sanitary napkin.

It is a further object of the present invention to provide an absorbent article with such an improved distribution strip.

SUMMARY OF THE INVENTION

The present invention provides an absorbent article such as sanitary napkins, disposable diapers, and incontinent pads, having a rapid liquid distribution strip that provides improved distribution or wicking of liquid exudates. Such absorbent article comprising a liquid permeable topsheet, a liquid impermeable backsheet, a liquid absorbent pad and a liquid distribution strip. The absorbent pad is positioned between the topsheet and the backsheet and has longitudinal ends. The liquid distribution strip is positioned between the topsheet and the absorbent pad. The liquid distribution strip comprises a nonwoven web which has a screen pattern comprising high fiber density portions with reduced spacing between the fibers, or has an embossed pattern having highly compressed portions, or has both a screen pattern and an embossed pattern. The high fiber density portions of the screen pattern are oriented primarily to the longitudinal ends of the absorbent pad so as to distribute liquid to the longitudinal ends. The highly compressed portions of the embossed pattern are oriented primarily to the longitudinal ends so as to inhibit the distribution of fluid toward the lateral edges.

DETAILED DESCRIPTION OF THE INVENTION

Figure 1:
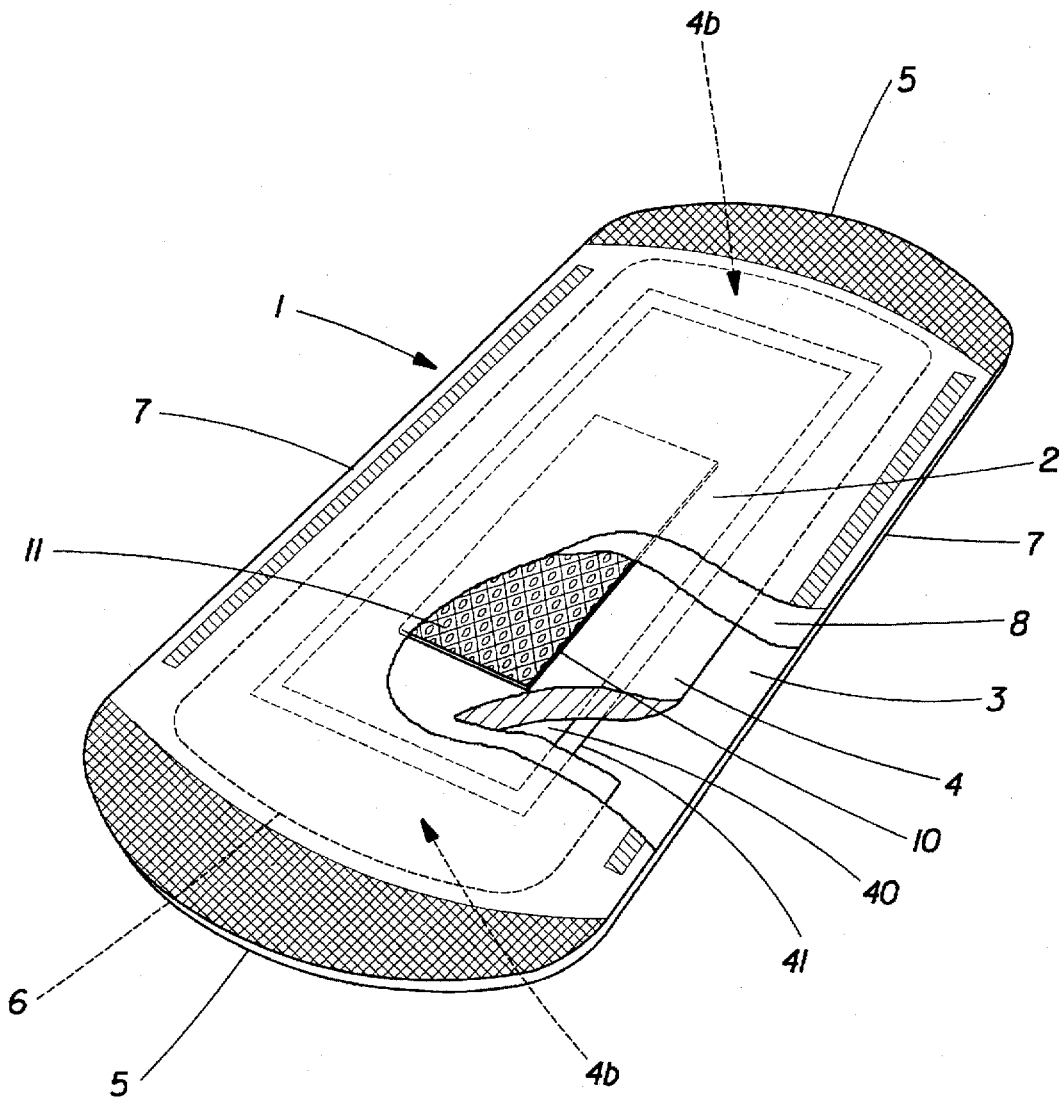
FIG. 1 is a perspective view of a sanitary napkin embodiment of the present invention having a portion cut away to reveal underlying structure.

As shown in FIG. 1, the absorbent article 1 is usually substantially rectangular as a whole, though the end edges can be arc portions 5, respectively. The absorbent member 4 is generally smaller than the backsheet and is substantially rectangular, though both end edges are in the form of an arc portion 6 which pattern after the arc portion 5 of the backsheet 3, and both longer sides 7 of the absorbent pad 4 are curved inward so that the center portion becomes slightly narrow.

The absorbent article 1 has two centerlines: a longitudinal centerline and a transverse centerline. The term "longitudinal", as used herein, refers to a line, axis or direction in the plane of the absorbent article 1 that is generally aligned with (e.g., approximately parallel to) a vertical plane which bisects a standing wearer into left and right body halves when the absorbent article 1 is worn. The terms "transverse" or "lateral" as used herein, are interchangeable, and refer to a line, axis or direction which lies within the plane of the absorbent article 1 that is generally perpendicular to the longitudinal direction.

The topsheet is generally registered to cover completely the wearer-facing surface of the absorbent pad. Preferably, the topsheet extends beyond the periphery of the absorbent pad, or wraps around the lateral edges of the absorbent pad, and can be secured to the backsheet around the periphery to enclose the absorbent pad.

One embodiment of an absorbent article 1 according to this invention is shown in FIG. 1. The absorbent article 1 comprises a liquid permeable topsheet 2, a liquid impermeable backsheet 3, a liquid absorbent pad 4 for absorbing a liquid exuded from the human body positioned therebetween, and a liquid distribution strip 10 for distributing the liquid exudates in the generally longitudinal direction. The phrase "generally longitudinal direction", as used herein, is intended to include angled direction from the longitudinal centerline. The term "primarily" is used herein as the same of the term "generally" not to limit to a specific angle or direction. A preferred absorbent article 1 optionally comprises a secondary layer between the topsheet 2 and the backsheet 3.

While the topsheet 2, the backsheet 3, and the absorbent core 4 can be assembled in a variety of well known configurations (including so called "tube" products or side flap products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; and U.S. Pat. No. 4,589,876, "Shaped Sanitary Napkin With Flaps" issued to Van Tilburg on Aug. 18, 1987. Each of these patents is incorporated herein by reference. FIG. 1 shows a preferred embodiment of the sanitary napkin in which the topsheet 2 and the backsheet 3 have length and width dimensions generally larger than those of the absorbent core 4. The topsheet 2 and the backsheet 3 can extend beyond the edges of the absorbent core 4 thereby forming not only portions of the periphery but also side flaps.

In a preferred embodiment of the present invention, the distribution strip 10 is positioned between the topsheet 2 and the absorbent core 4. In another preferred embodiment of the present invention, a distribution strip 10 is positioned between the topsheet 2 and an air-laid tissue 8 which serves as a secondary layer positioned on the absorbent core 4. The distribution strip 10 is arranged at the middle portion 4a between the longitudinal ends 4b and generally centered between the sides of the absorbent core. The distribution strip 10 provides permeability and diffusivity of the liquids into and along the longitudinal length of the absorbent core.

Figure 2:
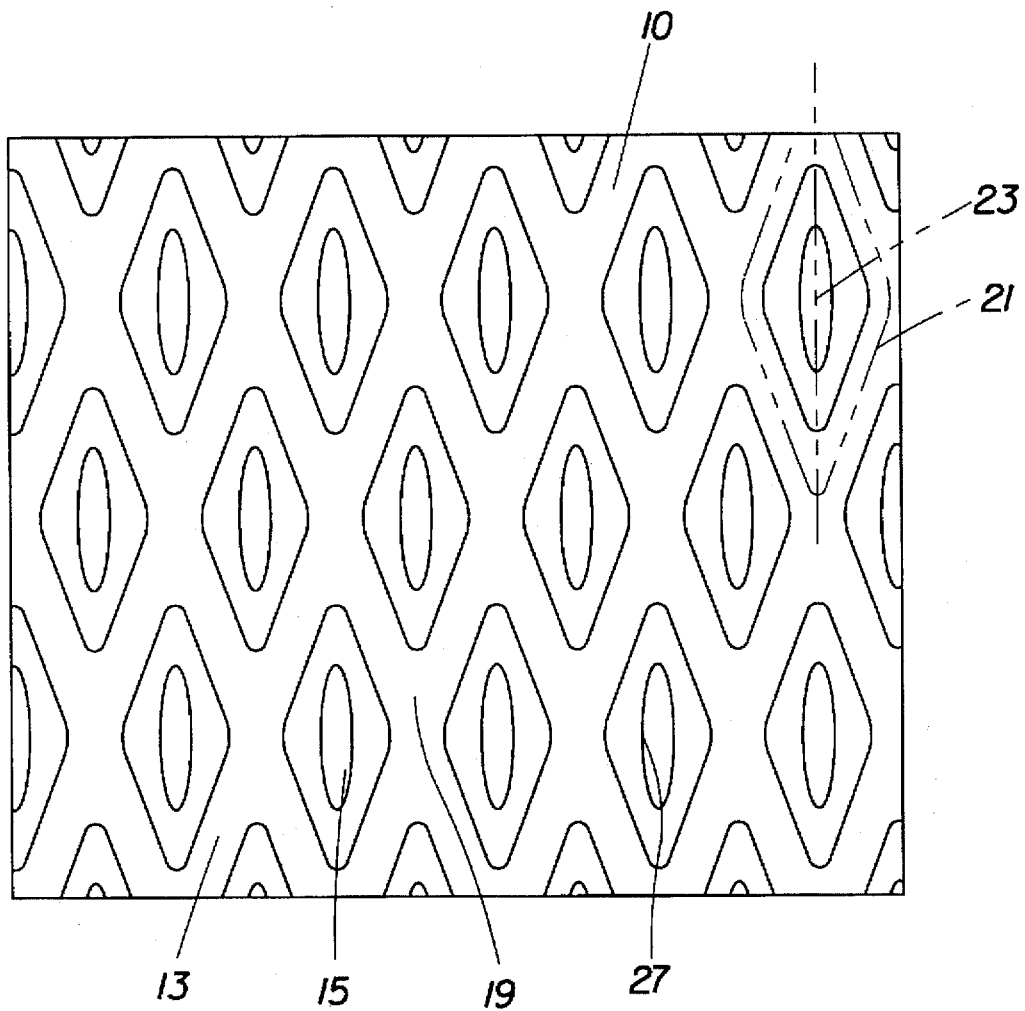
FIG. 2 is a top plane view of the distribution strip of the present invention shown in FIG. 1, the topsheet side facing the viewer.
Figure 3:
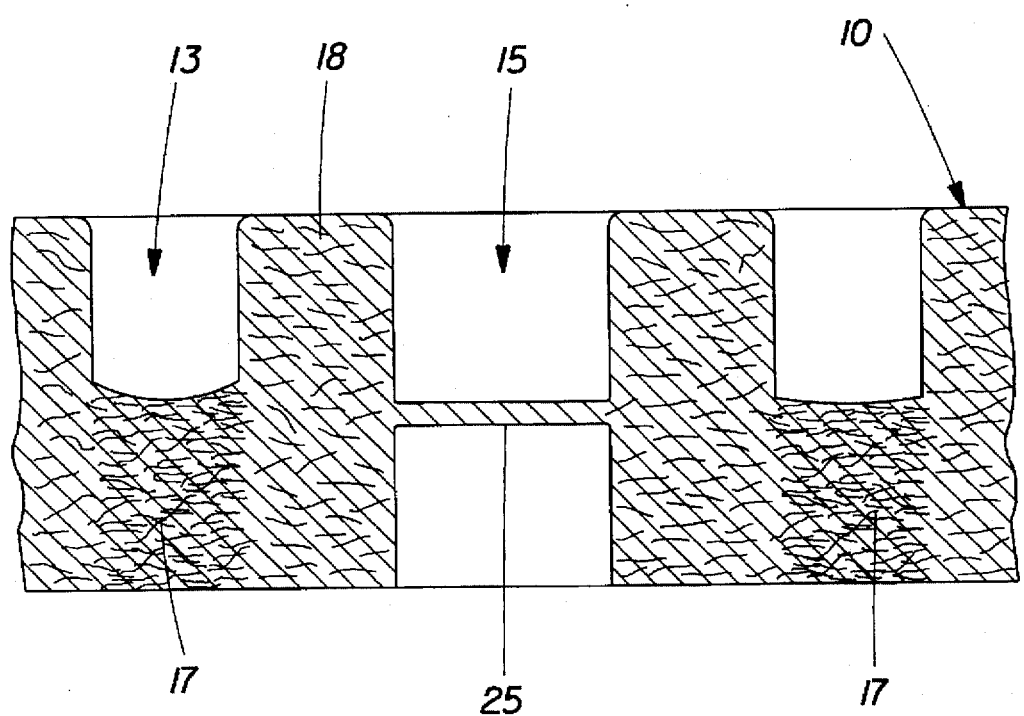
FIG. 3 is an enlarged cross-sectional view taken along line 3—3 of FIG. 2.

The distribution strip 10 of the present invention is shown in FIGS. 1 to 3. In the preferred embodiment, the distribution strip 10 is a rectangular strip in plan view. It should be understood, however, that the distribution strip need not be a strip. The term "strip", as used herein, include, but is not limited to single unfolded sheets, folded sheets, strips of material, sheets having loose or bonded fibers, multiple layers or laminates of material, or other combinations of such materials. Furthermore, the distribution strip 10 need not have a rectangular shape. The term "strip", as used herein again, include, but is not limited to a rectangular shape, a dog-bone shape, an hourglass shape, and a triangular shape.

For an absorbent core 4 having a lateral width of about 60 mm, the width of the distribution strip 10 is preferably about 20 mm to 40 mm, more preferably about 30 mm. The ratio of the width of the distribution strip 10 to the lateral width of the absorbent core 4 can vary based on the liquid wicking rate of the distribution strip and the absorbent capacity of the absorbent core 4. The ratio is preferably about 1:6 to 5:6, more preferably about 2:5 to 7:10. The length of the distribution strip 10 is preferably smaller than the length of the absorbent core 4 in the longitudinal direction. For an absorbent core 4 having a length in the longitudinal direction of about 180 mm, the length of the distribution strip 10 is preferably about 110 mm. It has been found that such shapes and size of the distribution strip is desirable from a product performance, process, and aesthetics standpoint.

The distribution strip 10 comprises a nonwoven web which has a visible pattern 11 on the surface oriented primarily in the longitudinal direction. The visible pattern 11 characterizes the direction of liquid distribution in a distribution strip 10 of the present invention from that of a nonwoven material in general having uniform fiber density and structure. Nonwoven materials in general transport liquids at the same rate in all directions (i.e., in the x-y plane and in the z-direction).

The visible pattern 11 can be a screen pattern 13 or an embossed pattern 15, preferably a combination of the screen pattern 13 and the embossed pattern 15. As shown in FIG. 3, the screen pattern 13 comprises high fiber density portions 17 oriented primarily in the longitudinal direction to the longitudinal ends of the napkin. The high fiber density portions are those portions of the nonwoven wherein the nonwoven is compressed in the vertical or Z-direction. In a preferred embodiment, the screen pattern 13 comprises a lattice pattern 19 comprising a rhombus 21 having a long axis 23 and a short axis wherein the long axis of each rhombus is oriented in the longitudinal direction to the longitudinal ends of the napkin. The term "screen pattern" as used herein also includes but is not limited to plural substantially parallel lines, plural lines comprising repeated elements of a long line and a short line, a herringbone pattern, or continuous and/or discontinuous pattern of such lines and patterns, or combinations of such patterns oriented primarily in the longitudinal direction.

The screen pattern can be made in the process of binding fibers into meltblown nonwovens. In the binding step of the process, melted thermoplastic resins is flown off with a high speed gas stream from a die tip of an extruder onto a conveyer or a collecting screen and forming a web of randomly oriented fibers. As shown in FIG. 3, the surface projected configuration of the conveyer or the collecting screen makes a concaved screen pattern 13 in the nonwoven wherein the fibers are spaced more closely together and the density of the fibers is relatively higher at the screen pattern 13 than at the remaining portions of the nonwoven. The concaved screen pattern 13 comprises high fiber density portions having narrow spaces between the fibers to provide excellent capillarity, such that the liquid distribution speed in the concaved portion is higher than an uncompressed portion 19. Since the distribution strip 10 in this embodiment has a lattice pattern 19 and each rhombus's long axis 23 is oriented in the longitudinal direction, the liquid distribution rate in the longitudinal axis exceeds the distribution rate in the lateral direction.

The embossed pattern 15 of the visible pattern 11 comprises the portion wherein the nonwoven fibers are highly compressed into a thin film segment 25 which inhibits liquid distribution through the embossed pattern 15. In a preferred embodiment, the embossed pattern 15 comprises slender ellipses 27 where the fibers of the nonwoven are highly compressed or are stamped or punched through. The slender ellipses 27 are positioned at regular intervals over the distribution strip, most particularly in the center portion and near the lateral edges. Each slender ellipse 27 is oriented preferably in the longitudinal direction. It should be understood, however, that the embossed patterns 15 need not be a slender ellipses pattern 27 oriented in the longitudinal direction. The term "embossed pattern" as used herein also includes, but is not limited to straight lines, curved lines, or continuous and/or discontinuous patterns of such lines, or other patterns oriented primarily in the longitudinal direction. The embossed pattern can be made by applying pressure and heat energy onto one, preferable both, surfaces of a portion of a nonwoven by a pair of embossment rollers. The thin film segment 25 of the embossed portion inhibits the distribution of liquid through the embossed portion such that substantially all of the liquid must distribute around the embossed pattern 27.

The combination of the screen pattern 13 and embossed pattern 15 provides the superior liquid distribution in the longitudinal direction because of good liquid diffusion rate in the longitudinal direction at the screen pattern and inhibits liquid distribution in the lateral direction at the embossed pattern 15. The screen pattern 13 and the embossed pattern 15 can also be combined randomly. In the preferred embodiment, the embossed pattern 15 is combined inbetween the concave line segment 13a of the screen pattern 13, which provides superior liquid distribution by combining the different character of each the screen pattern 13 and the embossed pattern 15.

The distribution strip 10 is preferably hydrophilic in order to provide good distribution and wicking of the liquid passing into and through it. The fibers or yarns forming the distribution strip can be inherently hydrophilic, though in such case, it is preferred that they can be further treated to render their surface hydrophilic. Suitable methods for rendering fibers hydrophilic include treating them with a surfactant. The fibers can be treated by spraying the material forming the distribution strip 10 with a surfactant or immersing the material into the surfactant. A more detailed discussion of such a treatment and hydrohilicity is contained in U.S. Pat. Nos. 4,988,344 and 4,988,345 issued to Reising, et al. and to Reising, respectively.

The distribution strip 10 can be a woven or nonwoven material. This material can be synthetic, or partially synthetic and partially natural material. Suitable synthetic fibers include polyester, polypropylene, polyethylene, nylon, viscous rayon fibers, or cellulose acetate, with polyester fibers being preferred. Suitable natural fibers include cotton, cellulose, or other natural fibers. The distribution strip 10 can also at least partially comprise cross-linked cellulose fibers. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1989 to Moore, et al.; and U.S. Pat. No. 4,935,022 issued Jun. 19, 1990 to Lash et al. The quantity of such natural or modified fibers, however, should not be so great that the topsheet cannot be adequately fused to the remaining synthetic fibers. The distribution strip can also comprise capillary channel fibers (that is, fibers having channels formed therein, preferably, on their exterior surfaces). Such fibers are described in greater detail in EPO Patent Application 0 391,814 published Oct. 10, 1990, and in the Capillary Channel Fiber patent applications. The distribution strip can also comprise combinations of the above materials, such as blends of fibers similar to those described below for use in the absorbent core, or any equivalent material or combinations of materials.

The distribution strip 10, if nonwoven, can be made by a number of different processes, including, but are not limited to, spunbonding and carding. In a particularly preferred embodiment, the distribution strip comprises a meltblown nonwoven web. Preferably, the distribution strip has a basis weight of about 50 to 100, preferably about 90 gms/m2, of polyethylene meltblown nonwoven web. Meltblown fabrics of this type are manufactured by Scott Nonwovens, Scott Paper Company of Philadelphia, Pa., the U.S.A.. The meltblown nonwoven web comprises fine, small-diameter fibers which create tiny spaces between fibers, which promote liquid wicking. The fibers or yarns comprising the distribution strip can be of any length, from staple length to continuous filaments. The fibers preferably have a denier under 1.0, more preferably averaged about 0.52.

The fibers of this particularly preferred distribution strip material are made of a polyethylene resin. The preferred topsheet made of a polyethylene resin facilitates the fusion bonding to the distribution sheet. In a preferred embodiment, the distribution strip can be maintained in contact with the topsheet by any of the conventional means for joining webs together such as mechanical bonding and adhesive attachment means, most preferably by fusion bonding as described in the U.S. patent application Ser. No. 07/810,774, now abandoned in the names of Cree, et al. The fusion bonding includes heat bonding, ultrasonic bonding, and the like.

Figure 4:
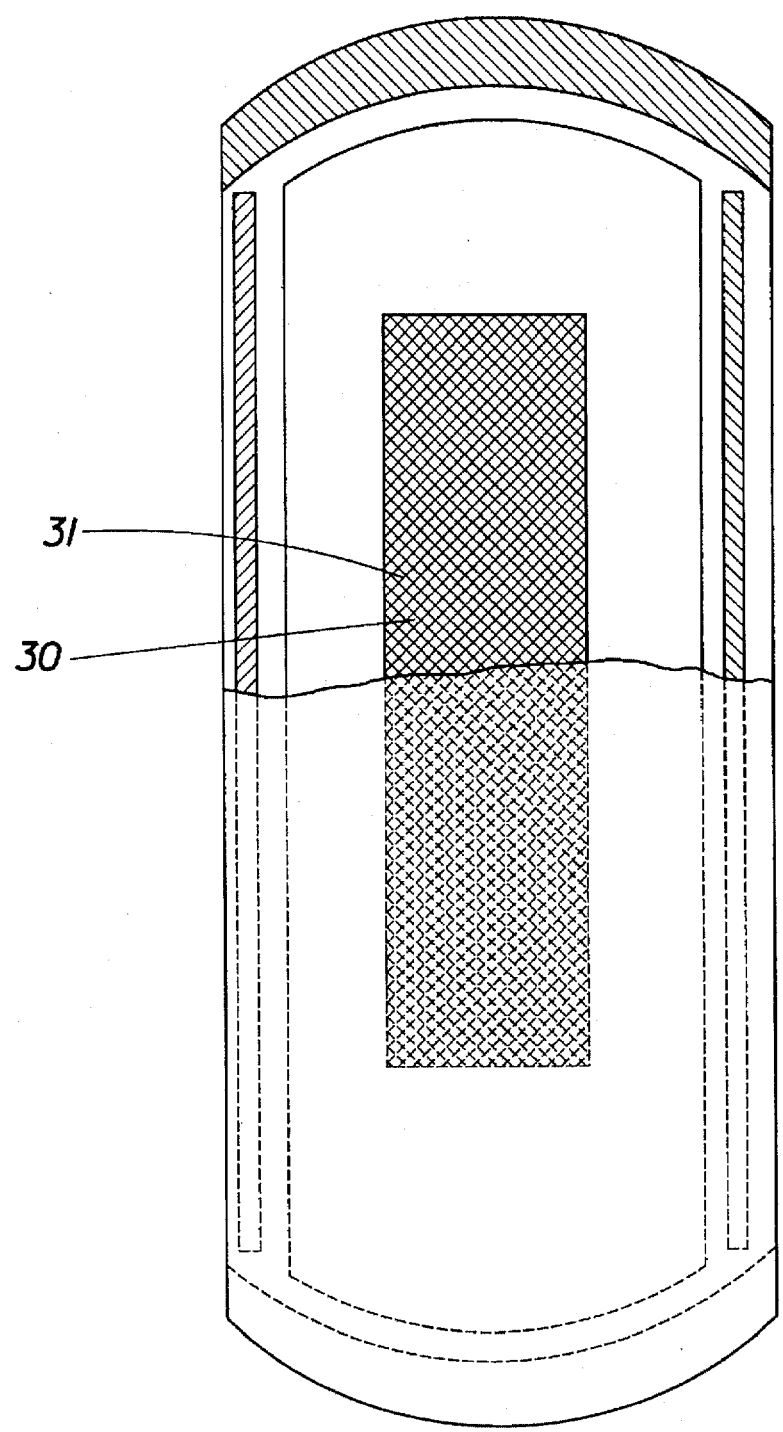
FIG. 4 is an alternative sanitary napkin embodiment of the present invention.

In another embodiment of the present invention shown in FIG. 4, distribution strip 30 is melt-blown or spun-bond non-woven, and provides enhanced liquid distribution in the longitudinal direction of the absorbent article. A particularly preferred distribution strip 30 comprises a series of longitudinally-oriented embossments or compressments. In the particular embodiment, the series of longitudinally-oriented embossments or compressments forms a lattice pattern 31 having rhombuses 33. The size and shape of the distribution strip 30 should be determined to be desirable from a product performance, and aesthetics standpoint. Preferably, the distribution strip 30 has a z-direction thickness or caliper of about 0.55 to 0.58 mm, a width of about 30 mm, and a length of about 110 mm.

The longitudinal end edge portion 5 of the absorbent article 1 is typically formed by joining together the topsheet 2 and the backsheet 3, as well as any additional non-woven fabric layer 15, with a suitable seal 8, preferably a heat seal.

The backsheet 3 and topsheet 2, and any additional non-woven fabric layer 15 as applicable, can be secured to the absorbent core 4 by attachment means (not shown) such as those well known in the art. For example, the backsheet 3 and/or the topsheet 2 can be attached to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means can comprise heat bonds, pressure bonds, ultrasonic bonds, dynamic mechanical bonds, or any other suitable attachment means or combinations of these attachment means as are known in the art.

The topsheet 2 is compliant, soft feeling, and non-irritating to the wearer's skin. Further, the topsheet 2 is liquid pervious permitting liquids (e.g., menses and/or urine)

to readily penetrate through its thickness. A suitable topsheet 2 can be manufactured from a wide range of materials such as woven and non-woven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these references are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., now abandoned, which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

The backsheet 3 is impervious to liquids (e.g., menses and/or urine) and is preferably manufactured from a thin plastic film, although other flexible liquid impervious materials can also be used. As used herein, the term "flexible" refers to materials which are compliant and will readily conform to the general shape and contours of the human body. The backsheet 3 prevents the exudates absorbed and contained in the absorbent core 4 from wetting articles which contact the sanitary napkin such as pants, pajamas and undergarments. The backsheet 3 can thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 3 can permit vapors to escape from the absorbent core 4 (i.e., breathable) while still preventing exudates from passing through the backsheet 3.

The absorbent pad 4 is any absorbent means which is capable of absorbing or retaining liquids (e.g., menses and/or urine). As discussed above, the absorbent core 4 can be manufactured in a wide variety of sizes and shapes (e.g., rectangular, oval, hourglass, dog bone, asymmetric, etc.) and from a wide variety of liquid-absorbent materials commonly used in absorbent napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core can also be varied. For example, the absorbent core can have varying caliper zones (e.g., profiled so as to be thicker in the center), hydrophilic gradients, superabsorbent gradients, or lower density and lower average basis weight acquisition zones; or can comprise one or more layers or structures. The total absorbent capacity of the absorbent core should, however, be compatible with the design loading and the intended use of the absorbent article. Further, the size and absorbent capacity of the absorbent core can be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

In use, the sanitary napkin 1 can be held in place by any support means or attachment means (not shown) well-known for such purposes. Preferably, the sanitary napkin is placed in the user's undergarment or panty and secured thereto by a fastener such as an adhesive 40. The adhesive 40 provides a means for securing the sanitary napkin in the crotch portion of the panty. Thus, a portion or all of the garment-facing surface of the absorbent article 1 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive is typically covered with a removable release liner 41 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 1 of the present invention is used by removing the release liner and thereafter placing the sanitary napkin in a panty so that the adhesive contacts the panty. The adhesive 40 assists in maintaining the sanitary napkin in its position within the panty during use.

In another preferred embodiment of the present invention, the sanitary napkin can have two flaps (not shown) each of which are adjacent to and extend laterally from a line of juncture located along the side edge of the absorbent core. The wings are configured to drape over the edges of the wearer's panties in the crotch region so that the wings are disposed between the edges of the wearer's panties and the thighs. The wings serve at least two purposes. First, the wings help to prevent soiling of the wearer's body and panties by menstrual fluid, preferably by forming a double wall barrier along the edges of the panty. Second, the wings are preferably provided with attachment means on their garment surface so that the wings can be folded back under the panty and attached to the garment facing side of the panty. In this way, the wings serve to keep the sanitary napkin properly positioned in the panty. The wings can be constructed of various materials including materials similar to the topsheet 2, backsheet 3, or combination of these materials. Further, the wings can be a separate element attached to the main body of the napkin, or can comprise extensions of the topsheet 2 and backsheet 3 (i.e., unitary). A number of sanitary napkins having wings suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

As clearly seen from the above illustration, according to this invention, the liquid distribution strip improves wicking of liquid exudates over and into the absorbent core and allows the absorbent article to be made relatively thin. Thus, the present invention provides a liquid distribution strip having improved liquid distributing characteristics and also provides an absorbent article with such an improved distribution strip having improved leakage prevention along the lateral edges.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for absorbing a liquid exuded from a human body, said absorbent article having a longitudinal centerline defining a longitudinal direction and a lateral centerline defining a lateral direction and comprising a liquid permeable topsheet, a liquid impermeable backsheet, a liquid absorbent pad positioned therebetween and having longitudinal ends, and a liquid distribution strip being positioned between said topsheet and said absorbent pad, said liquid distribution strip comprising a nonwoven web having portions of said web compressed into areas of high fiber density and also having portions of said web compressed from both sides of said web into thin film segments of a density greater than that of said high fiber density areas, such that substantially all of said liquid distributes around said thin film segments.

2. The absorbent article of claim 1, wherein said areas of high fiber density form a continuous pattern.

3. The absorbent article of claim 2 wherein said continuous pattern comprises a plurality of parallel lines.

4. The absorbent article of claim 2 wherein said continuous pattern comprises a lattice pattern having rhombuses, each rhombus having a long axis, said long axis being oriented in said longitudinal direction.

5. The absorbent article of claim 4 wherein said thin film segments comprise a plurality of slender ellipses disposed within said rhombuses, each of said rhombuses having a single ellipse disposed therein.

6. The absorbent article of claim 1 wherein said thin film segments comprise a plurality of discontinuous lines.

7. An absorbent article for absorbing a liquid exuded from a human body, said absorbent article having a longitudinal centerline defining a longitudinal direction and a lateral centerline defining a lateral direction, longitudinal edges, and lateral edges, said absorbent article comprising a liquid permeable topsheet, a liquid impermeable backsheet, a liquid absorbent pad positioned therebetween and having longitudinal ends, and a liquid distribution strip being positioned between said topsheet and said absorbent pad, said liquid distribution strip comprising a fibrous nonwoven web having an embossed pattern which comprises said web being compressed from both sides forming embossed portions oriented primarily in the longitudinal direction wherein said fibers of said embossed portions are highly compressed forming a thin film segment so as to inhibit the distribution of said body liquid in said lateral direction.

* * * * *

UNITED STATES PATENT AND TRADEMARK OFFICE
CERTIFICATE OF CORRECTION

| | | |
|---|---|---|
| PATENT NO. | : 5,669,895 | |
| APPLICATION NO. | : 08/232243 | |
| DATED | : September 23, 1997 | |
| INVENTOR(S) | : Setsuko Murakami et al. | |

It is certified that error appears in the above-identified patent and that said Letters Patent is hereby corrected as shown below:

Column 9, Line 9, please delete "Silcox E1/0" and insert therefor --Silcox EI/O--.

Column 9, Line 10, please delete "Silcox 4P/0" and insert therefor --Silcox 4P/O--.

Column 10, Line 41 (Claim 7), please delete "direction and a" and insert therefor --direction, a--.

Signed and Sealed this

Seventeenth Day of July, 2007

JON W. DUDAS
*Director of the United States Patent and Trademark Office*